(12) United States Patent
Kajava

(10) Patent No.: US 11,568,082 B2
(45) Date of Patent: Jan. 31, 2023

(54) METHOD AND SYSTEM FOR SECURING SENSITIVE INFORMATION

(71) Applicant: Megical Oy, Helsinki (FI)

(72) Inventor: Tuomo Kajava, Helsinki (FI)

(73) Assignee: MEGICAL OY, Helsinki (FI)

(*) Notice: Subject to any disclaimer, the term of this patent is extended or adjusted under 35 U.S.C. 154(b) by 593 days.

(21) Appl. No.: 16/658,578

(22) Filed: Oct. 21, 2019

(65) Prior Publication Data

US 2021/0117566 A1  Apr. 22, 2021

(51) Int. Cl.
| | |
|---|---|
| G06F 21/62 | (2013.01) |
| G16H 10/60 | (2018.01) |
| H04L 9/08 | (2006.01) |
| H04L 9/40 | (2022.01) |

(52) U.S. Cl.
CPC ......... *G06F 21/6245* (2013.01); *G16H 10/60* (2018.01); *H04L 9/0825* (2013.01); *H04L 63/083* (2013.01); *H04L 63/0823* (2013.01)

(58) Field of Classification Search
CPC ..... G06F 21/6245; G06F 21/34; G16H 10/60; G16H 80/00; G16H 10/65; H04L 9/0825; H04L 63/0823; H04L 63/083; H04L 9/3234
USPC .......................................................... 705/2–3
See application file for complete search history.

(56) References Cited

U.S. PATENT DOCUMENTS

| | | | |
|---|---|---|---|
| 9,419,951 B1* | 8/2016 | Felsher | H04L 9/0841 |
| 10,841,286 B1* | 11/2020 | Davidovics | H04L 9/3247 |
| 10,943,680 B1* | 3/2021 | Knas | H04L 9/0861 |
| 2016/0005032 A1* | 1/2016 | Yau | G06Q 20/3674 |
| | | | 705/69 |
| 2019/0036688 A1* | 1/2019 | Wasily | H04L 9/0825 |
| 2019/0095655 A1 | 3/2019 | Krawczewicz et al. | |
| 2020/0211409 A1* | 7/2020 | Latorre | H04L 9/0861 |
| 2020/0329017 A1* | 10/2020 | Kim | A61B 5/002 |
| 2021/0366586 A1* | 11/2021 | Ryan | G06Q 20/389 |

(Continued)

OTHER PUBLICATIONS

M. Li, S. Yu, and Y. Zheng, "Scalable and secure sharing of personal health records in cloud computing using attribute-based encryption," IEEE Transactions on Parallel and Distributed Systems, vol. 24, No. 1, pp. 131-143, 2012. (Year: 2012).*

(Continued)

*Primary Examiner* — Joshua B Blanchette
(74) *Attorney, Agent, or Firm* — Ziegler IP Law Group

(57) ABSTRACT

A method for securing sensitive information, includes storing patient information in a secured form in an external device that is carried by a patient. A user terminal obtains a first signature generated using a first secret key inside a first identification medium, where the first secret key is associated with a first healthcare person. Moreover, the user terminal communicates a write request that includes at least the first signature to the external device. The external device receives the write request from the user terminal when the user terminal is within a proximal communication range of the external device. Furthermore, the external device verifies at least the first signature received in the write request. The user terminal writes first information to the external device, based on verification of at least the first signature. A system for securing sensitive information is also provided.

18 Claims, 5 Drawing Sheets

(56) References Cited

U.S. PATENT DOCUMENTS

2021/0375408 A1* 12/2021 Krueger .............. G06Q 20/401

OTHER PUBLICATIONS

Aboelfotoh et al. "A mobile-based architecture for integrating personal health record data", 2014 IEEE 16th International Conference On E-Health Networking, Applications and Services (Healthcom), IEEE. pp. 269-274, XP032715847, DOI: 10.1109/HEALTHCOME.2014.07001853, Oct. 15, 2014, 6 pages.
European Patent Office, Extended European Search Report, Application No. 20201027.8, dated Mar. 18, 2021, 12 pages.

\* cited by examiner

METHOD AND SYSTEM FOR SECURING SENSITIVE INFORMATION

TECHNICAL FIELD

The present disclosure relates generally to data security; and more specifically, to methods and systems for securing sensitive information.

BACKGROUND

Generally, higher level of controls and security measures are required to manage sensitive information as compared to non-sensitive information. The sensitive information refers to privileged information that needs to be protected from unauthorized access to safeguard the privacy or security of an individual or organization. An example of the sensitive information is health or medical information. Typically, the medical information is maintained in the form of physical documents, such as hand-written prescriptions, X-ray reports, MRI scans, and so forth. However, such physical documents may get damaged over a period of time and thus the medical information is susceptible to loss. Therefore, to overcome drawbacks associated with the physical documents, nowadays the medical information is stored as electronic data in order to ensure that the information is available to healthcare personnel whenever needed to be able to provide proper medical care to a patient. Notably, the electronically stored medical information of a patient is considered sensitive information that needs to be safeguarded from unauthorized access and editing. The safeguarding of the electronic medical information is paramount to ensure that the sensitive information is protected from the threat of theft and privacy breaches.

Currently, there are many technical problems associated with storing and processing of the sensitive information, such as the sensitive medical information. The processing of sensitive information is technically challenging because of the laws, regulations and other principles that demands to meet requirements of security of such sensitive information. Moreover, in addition to security, availability of the sensitive information is also a primary requirement for practical real-world applications. For example, in provisioning of medical care, patient information must be available all the time. However, under certain circumstances, the availability as well as security of the patient information may not be achieved concurrently using conventional systems and methods. For example, sensitive information may be stored in server systems, and a network connectivity to such server system may be temporality unavailable or there may be issues in the network connectivity causing interruptions in patient care, which is not desirable. Further, an unauthorized access of such sensitive information in such critical circumstances may result in sacrifice of patient safety or overlook strict security requirements, which is not desirable.

Therefore, in light of the foregoing discussion, there exists a need to overcome the aforementioned drawbacks associated with the conventional systems and methods that process sensitive information.

SUMMARY

The present disclosure seeks to provide a method for securing sensitive information. The present disclosure also seeks to provide a system for securing sensitive information. The present disclosure seeks to provide a solution to the existing problem of inadequate availability and security risk related to processing of sensitive information. An aim of the present disclosure is to provide a solution that overcomes at least partially the problems encountered in prior art, and provides a method and a system that adequately secures sensitive information (from reading and unauthorized editing) and at the same time ensures all-time availability of the sensitive information for authorized person.

In one aspect, an embodiment of the present disclosure provides a method for securing sensitive information, the method comprising:

storing patient information in a secured form in an external device that is carried by a patient;

obtaining, by the user terminal, a first token from a server system and a first signature generated using a first secret key inside a first identification medium, wherein the first secret key is associated with a first healthcare person;

communicating, by the user terminal to the external device, a write request that includes at least the first signature and the first token;

receiving, by the external device, the write request from the user terminal when the user terminal is within a proximal communication range of the external device;

verifying, by the external device, at least the first token received in the write request; and writing, by the user terminal, a first information to the external device, based on verification of at least the first token.

In another aspect, an embodiment of the present disclosure provides a system for securing sensitive information, the system comprising:

an external device configured to store patient information in a secured form, wherein the external device is carried by a patient;

a user terminal that is configured to:

obtain a first token from a server system and a first signature generated using a first secret key inside a first identification medium, wherein the first secret key is associated with a first healthcare person;

communicate a write request that includes at least the first signature and the first token to the external device;

wherein the external device is configured to:

receive the write request from the user terminal when the user terminal is within a proximal communication range of the external device; and verify at least the first token received in the write request; and the user terminal is further configured to write a first information to the external device, based on verification of at least the first token.

In yet another aspect, an embodiment of the present disclosure provides a computer program product comprising a non-transitory computer-readable storage medium having computer-readable instructions stored thereon, the computer-readable instructions being executable by a computerized device comprising processing hardware to execute the abovementioned method.

Embodiments of the present disclosure substantially eliminate or at least partially address the aforementioned problems in the prior art, and ensures that the sensitive information is available all-the-time but only to authorized healthcare persons regardless of network and/or server connections, and at the same time meets the security requirements related to storage, sharing, and processing of such sensitive information. Thus, the all-time availability of such sensitive information in a secured manner ensures proper decision support for an authorized healthcare person to provide adequate and better care to the patient.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1A:
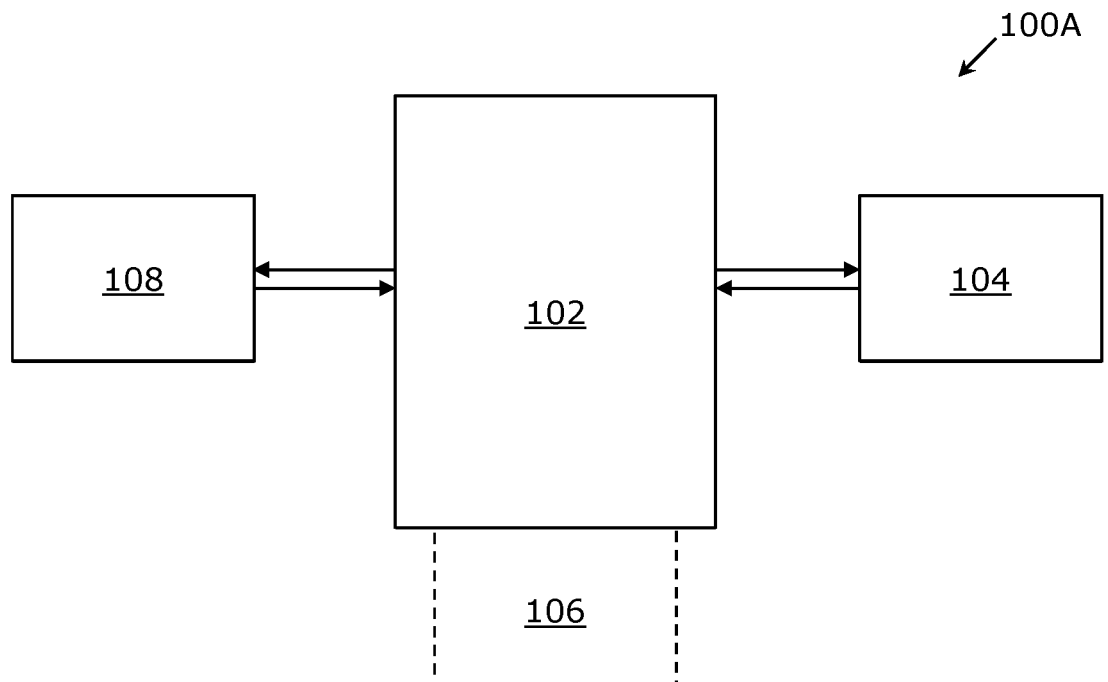
FIG. 1A is a block diagram of a system to secure sensitive information, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practising the present disclosure are also possible.

In one aspect, an embodiment of the present disclosure provides a method for securing sensitive information, the method comprising:
  storing patient information in a secured form in an external device that is carried by a patient;
  obtaining, by the user terminal, a first token from a server system and a first signature generated using a first secret key inside a first identification medium, wherein the first secret key is associated with a first healthcare person;
  communicating, by the user terminal to the external device, a write request that includes at least the first signature and the first token;
  receiving, by the external device, the write request from the user terminal when the user terminal is within a proximal communication range of the external device;
  verifying, by the external device, at least the first token received in the write request; and
  writing, by the user terminal, a first information to the external device, based on verification of at least the first token.

In another aspect, an embodiment of the present disclosure provides a system for securing sensitive information, the system comprising:
  an external device configured to store patient information in a secured form, wherein the external device is carried by a patient;
  a user terminal that is configured to:
    obtain a first token from a server system and a first signature generated using a first secret key inside a first identification medium, wherein the first secret key is associated with a first healthcare person;
    communicate a write request that includes at least the first signature and the first token to the external device;
  wherein the external device is configured to:
    receive the write request from the user terminal when the user terminal is within a proximal communication range of the external device; and
    verify at least the first token received in the write request; and the user terminal is further configured to write a first information to the external device, based on verification of at least the first token.

In yet another aspect, an embodiment of the present disclosure provides a computer program product comprising a non-transitory computer-readable storage medium having computer-readable instructions stored thereon, the computer-readable instructions being executable by a computerised device comprising processing hardware to execute the aforementioned method.

The present disclosure provides a method and a system to secure sensitive information. The system comprises an external device that is capable to securely store, transmit and receive the sensitive information, such as the patient information. The external device is allotted to a patient and is carried by the patient throughout a medical treatment. The system further comprises an identification medium that is allotted to a healthcare person. The identification medium acts as an authorization medium for each healthcare person such that only the authorized healthcare person is allowed to access the sensitive information. The external device is configured to store the sensitive information in a secured manner that may be presented, and new information may be added or accessed by authorized healthcare person using a combination of the user terminal and the identification medium in a secure way. In addition existing information in the external device can be updated in a secure way. Thus, the sensitive information is safeguarded from the threat of theft and privacy breaches. Furthermore, the authorized healthcare persons may securely and conveniently access or write new information to external device via a short-range communication with the user terminal, even in the absence of network connectively with a server system. Thus, the security as well as the all-time availability of the sensitive information is achieved by using the disclosed method and system.

The system for securing sensitive information comprises the aforementioned external device and the user terminal. Throughout the present disclosure, the term "external device" refers to a compact and portable electronic device having a secured physical area, such as a secure element (SE) to store the sensitive information in a secured form. The external device potentially includes a memory and a communication interface therein. The patient information stored in the external device may be read and new information related to a subject is written through the communication interface. The communication interface of the external device is configured to enable short-distance radio communication, for example Near Field Communication (NFC), Bluetooth, or wireless-fidelity (Wi-Fi). In an exemplary implementation, the communication interface of the external device is also configured to enable a long-range communication, such as cellular communication. Optionally, the external device may have a display. Examples of the external device include, but is not limited to a wristband, a key fob, a storage chip, and the like. The external device is configured to store, transmit, and receive the sensitive information in a secured form. Throughout the present disclosure, the term "user terminal" refers to an electronic device that comprises logic, circuitry, or interfaces configured to communicate with the external device, a server system, and the aforementioned identification medium. The user terminal typically comprises an operating system and a user interface. Furthermore, the user terminal is intended to be broadly interpreted to include any electronic device that may be used for communication of the sensitive information over a wired or wireless communication network. Examples of user terminal include, but are not limited to, a cellular phone, a personal digital assistant (PDA), a handheld electronic device, a laptop computer, a personal computer, and so forth.

According to an embodiment, the user terminal further comprises a communication interface and an application. The communication interface provides functionalities to communicate with external devices and networks using various communication protocol like NFC, Radio Frequency Identification (RFID), Bluetooth, Wi-Fi, Ethernet and the like. Further, the communication interface also enables long range radio communication with the server system using cellular communication, Internet, local area network (LAN), or wireless local area network (WLAN), and the like. Optionally, wired connections may be supported for both kind of communications (offline or online; short-range or long-range). Additionally, the user terminal may include a casing, a memory, a processor, a network interface, a display and so forth. The aforementioned application is usually pre-installed in the user terminal and facilitates various functions, such as registration of the user terminal, receiving new information as user input from a healthcare person that needs to be written in the external device, or other user-interaction for example, receipt of authorization data of healthcare person at the time of accessing the identification medium. Thus, the application refers to a software or a combination of software and hardware to generally provide user interface and logic to handle the sensitive information.

According to an embodiment, the system further comprises at least one identification medium and a server system. The "identification medium" refers to a medium that holds and protects user identities and/or device identities, authentication keys and additional operations to perform, for example, cryptographic functions. The identification medium may be an independent hardware device or it may be integrated with the user terminal as a software program. Optionally, the identification medium is potentially stored in a secured area within the user terminal when implemented as the software. Alternatively, the identification medium is implemented as a system on chip (SoC), or a combination of both the software and hardware. Physically, the identification medium may be a card, a wristband, a wristwatch, a chip or other kind of programmable media able to communicate with the user terminal, for example using appropriate card reader or NFC-radio, depending on the device capability of the user terminal for contactless communication. A distinct identification medium may be allotted to each healthcare person, such as a doctor or a nurse. In an embodiment, each identification medium may store unique information associated with the healthcare person, such as a name of the healthcare person, designation (or role) of the healthcare person, and the like. The "server system" refers to a structure and/or module that include programmable and/or non-programmable components configured to store, process and/or share information. Optionally, the server system includes any arrangement of physical or virtual computational entities capable of enhancing information to perform various computational tasks. Furthermore, it should be appreciated that the server system may be a single hardware server, a plurality of hardware servers operating in a parallel or distributed architecture or a cloud server. In an example, the server system may include components such as memory, a processor, a network adapter and the like, to store, process and/or share information with other computing components, such as the user terminal. Typically, the server system is protected using protected Application Program Interfaces (APIs) and secure connections to operate with the sensitive patient information. The server system is configured to manage and store patient information, user accounts, identification data such as user claims, certificate authority certificates and certificate revocation lists, functionalities for user terminal registration, initial key sharing and distribution protocols and the like.

The patient information is stored in a secured form in the external device that is carried by a patient. For example, initially, the external device may comprise a patient identifier associated with the patient, such as a social security number, a unique token assigned to the patient, and so forth. Optionally, the external device may also comprise basic information related to the patient, such as a name of the patient, an age of the patient, a gender of the patient, a contact number of the patient and so forth. Optionally, the external device may also comprise sensitive information associated with the patient, such as a medical history of the patient. Such external device comprising the patient information is allotted to the patient such that the external device is easily carried by the patient throughout a treatment process, for example, in a hospital.

According to an embodiment, the method for securing the sensitive information comprises executing registration of the user terminal (e.g. a mobile device) with the server system. The registration of the user terminal is performed by launching the pre-installed application in the user terminal by a healthcare person, such as a doctor or a nurse. Notably, the pre-installed application provides functionalities to the user terminal to communicate with the server system.

According to an embodiment, the method further comprises generating, by the user terminal, an asymmetric key pair in a registration phase of the user terminal to a server system. The registration of the user terminal to the server system is potentially facilitated by using an asymmetric cryptography technique. In such a technique, once the pre-installed application is launched, the asymmetric key pair is generated on the user terminal, that typically comprises two unidentical numeric keys paired together. One key in the key pair is a public key that is generally shared at least with the server system or other devices, whereas other key is a private key that is kept secret and only within the user terminal. The public key of the key pair generated during the registration phase is communicated to the server system and stored therein. The method comprises communicating, by the user terminal, a registration request that includes at least one of: a unique device identifier (ID) of the user terminal, or an application ID created by the application pre-installed in the user terminal, along with a device public key of the generated asymmetric key pair to the server system over a secured communication channel for registration of the user terminal at the server system. The user terminal communicates the registration request to the server system via a secured communication channel that may be for example, a dedicated communication channel or a secured cellular communication, or other secured communication, such as a wireless communication channel. The unique device ID may be, e.g., a sequence of alphanumeric characters that is distinct for each device. The user terminal communicates the registration request to the server system, such that the server system identifies and stores the unique device ID, the application ID and the device public key associated with the user terminal through which the registration request is communicated.

According to an embodiment, the method further comprises receiving, by the user terminal, validation data required for authorization decisions from the server system in response to the registration request communicated by the user terminal. Once the unique device ID, the application ID and the device public key are communicated to the server system, the server system communicates the validation data required for authorization decisions to the user terminal. The server system potentially comprises registered identities of the all the healthcare persons, having access to the patient information together with the data required to authorization decisions. In an example, while using the Public Key Infrastructure (PKI) based solution, trusted certificate authority certificates (CA), certificate revocation list (CRL) and public keys of the identity certificates (PKid) are stored to the server system. The validation data required for authorization decisions may be, e.g., device identity of the user terminal, trusted certificate authority certificates (CA), certificate revocation list (CRL), public keys of the identity certificates (PKid), list of identity (ID) of all the healthcare persons and so forth stored in the server system. The healthcare person, when in vicinity of the external device carried by the patient, enables the short-range communication between the user terminal and the identification medium for receiving authorization decisions based on the validation data. In an example, the first healthcare person inserts the first identification medium in a slot provided in the user terminal to enable the short-range communication for authorization purposes. Once the first identification medium is inserted in the slot of the user terminal, the user terminal obtains a first signature generated using the first secret key that is inside the first identification medium. The first secret key is associated with the first healthcare person. In order to initiate generation of the first signature, it may be required by the first healthcare person to first enter a pin-code, a password, or provide biometrics input and so forth via the user terminal. The pre-installed application checks proof of identity of the first healthcare person, for example, using the generated first signature (e.g. a digital signature) that is verified against public certificate presenting identity of the first healthcare person.

According to an embodiment, the method further comprises executing login, by the user terminal, to the server system based on login credentials comprising at least one of: user credentials that includes at least the first signature associated with the first healthcare person, device credentials of the user terminal, or a combination of the user credentials and the device credentials. The user credentials include at least the first signature associated with the first healthcare person obtained by the user terminal. Optionally, the user credentials include a username of the first healthcare person and a password associated with the username. The device credentials include the device ID of the user terminal, the application ID of the pre-installed application in the user terminal, the device secret key of the user terminal, and the like. In another example, digital signature-based methods like Fast Identity Online (FIDO) is used for authentication for login.

According to an embodiment, the method further comprises receiving, by the user terminal, up-to-date validation data from the server system based on a successful login of the user terminal to the server system, wherein the validation data comprises one or more of: a list of registered user identities, a list of roles of the registered user identities authorization certificates, and an access token. The list of registered user identities, such as the healthcare persons and optionally the list of their respective roles is received by the user terminal upon successful login. The role of each of the registered user identities refer to an authorization vector, that allows to set access control for information or any parts of the information to be processed by different roles. In an example, a first healthcare person is a doctor who is allowed to read and write the patient information. Thus, a role of the first healthcare person includes both reading and writing of the patient information. In another example, a second healthcare person is a nurse who is only allowed to read the patient information and not allowed update any new patient information. Thus, a role of the second healthcare person includes only reading the patient information. The authorization certificates, such as CA and CRL, are also received by the user terminal. The access token may include at least a session expiration time after which the user terminal logs out of the server system, an identification of the user, such as the username and so forth.

In an example, the first healthcare person may approach the patient who carries the external device with an intent to provide some medical care. Thus, when the external device is in vicinity of the user terminal (i.e. within a communication range), a short-range communication is established between the external device and the user terminal. After establishment of the short-range communication between the external device and the user terminal, the patient information stored in the external device is fetched from the external device by the pre-installed application in the user terminal. The first healthcare person is thus, allowed to access the received patient information based on the role of the first healthcare person, the access token, and the like. It will be appreciated that such a trusted chain between the system elements, such as the external device, the user terminal, the identification medium and the like ensures secure sharing of the sensitive patient information, as described below. The system and the method provide secure communication and storage of the sensitive information irrespective of availability of networks and the server system. The system and the method enable processing of the sensitive patient information via a signature-based verification process or a token-based verification process. The signature-based verification process uses a signature, such as the first signature, for authorization of the first healthcare person and the user terminal. On the other hand, the token-based verification process utilizes a token generated by the server system for authorization of the first healthcare person and the user terminal.

In the signature-based verification process, a signature that is representative of a successful verification of a personal identity of an authorized healthcare person and the devices used in handling of sensitive information, is used to either read existing patient information stored in secured form in the external device or write a new information related to the patient in the external device that is carried by a patient. The signature-based verification process is described below.

The method comprises obtaining, by the user terminal, a first token from a server system and the first signature generated using the first secret key inside the first identification medium, wherein the first secret key is associated with a first healthcare person. In a case where the first identification medium is a physical device, such as a smartcard, the first identification medium is introduced to the user terminal, for example, by inserting the first identification medium in a slot of the user terminal or by a contactless communication. The user terminal is configured to obtain the first token from a server system and the first signature which is generated using the first secret key that is inside the first identification medium. The first signature represents the first healthcare person. In a case where the first identification medium is a software integrated with the user terminal, the first signature is still fetched by the pre-installed application in the user terminal by establishing a communication with the first identification medium that stores the first secret key. The first token can be used for verification process. Typically a token is valid for determined amount of time.

Moreover, the method comprises communicating, by the user terminal to the external device, a write request that includes at least the first signature. The first healthcare person provides an input to the user terminal via the application of the user terminal to communicate a write request. The user terminal is configured to communicate the write request to update the prestored patient information in the external device. In an implementation, the write request that includes at least the first signature. In another implementation, the write request further includes a role (R) associated with first healthcare person, a public key of the user terminal, the authorization certificates, and a unique person identifier (ID_A) associated with the first identification medium together with the first signature.

The method further comprises receiving, by the external device, the write request from the user terminal when the user terminal is within a proximal communication range of the external device. The external device is configured to receive the write request initiated by the user terminal via the short-range communication.

Furthermore, the method comprises verifying, by the external device, at least the first token received in the write request. In an implementation, the external device verifies the write request based on at least the first token. In another implementation, the external device verifies other data items when received in the write request along with the token. For example, the role associated with first healthcare person, the public key of the user terminal, the authorization certificates, and the unique person identifier, and the like, are also verified by a software program stored in the secured area within the external device.

Moreover, the method comprises writing, by the user terminal, a first information to the external device, based on verification of at least the first token. The external device sets a state of the secured area in the external device as accept state, after successful verification of at least the first token received in the write request. For example, the first healthcare person is a doctor and based on examination of the patient, wants to write the observations or prescription directly into the external device using the user terminal after successful verification by the external device. Thus, the user terminal is configured to control writing of the first information (e.g. new patient information that is different than the stored patient information) in the external device. Optionally, the communication of the first information from the user terminal to the external device may be in a ciphered form.

According to an embodiment, the method further comprises obtaining, by the user terminal, a second token from a server system and a second signature generated using a second secret key that is in a second identification medium, wherein the second secret key is associated with a second healthcare person. If another healthcare person, such as the second healthcare person requires access of the latest patient information stored in the external device via the registered user terminal, the second healthcare person may present the second identification medium to the user terminal for authentication purposes. Similarly, the second signature generated from the second secret key present inside the second identification medium is obtained by the user terminal. Optionally, the user terminal may also perform login to the server system to retrieve up-to-date validation data from the server system. In deed with said setup a plurality of different healthcare persons can provide information (access, modify, add, edit) to the external device in a secure manner. Alternatively or additionally each or some of the healthcare persons can use same or different user terminals (i.e. different physical terminals).

According to an embodiment the method comprises communicating, by the user terminal, a read request to the external device, wherein the read request includes at least the second signature. The second healthcare person initiates the read request via the user terminal, to access the patient information stored in the external device. Optionally, if the server system connection is available, a new (second) token (T') is fetched after successful login and authentication of the second identification medium as validated by the server system. However, if the server system is not available, at least the second signature generated by the second identification, is communicated to the external device along the read request. In an implementation, similar to data items sent in the write request, a role associated with second healthcare person, the public key of the user terminal, the authorization certificates, and the unique person identifier associated with the second identification medium, and the like, are communicated in the read request to be verified by a software program stored in the secured area within the external device.

According to an embodiment the method further comprises verifying, by the external device, at least the second token communicated by the user terminal. In an implementation, the external device is configured to verify the read request based on at least the second signature or the second token representative of the second healthcare person who is in possession of the second identification medium.

According to an embodiment the method further comprises communicating, by the external device, updated patient information that includes the stored patient information and the first information to the user terminal for further processing based on a successful verification of at least the second token. The external device, after successful verification of at least the second token received in the read request, communicates the updated patient information that includes the stored patient information and the first information to the user terminal for further processing. The second healthcare person is thus, able to access the updated patient information via the user terminal. Optionally, the communication of the updated patient information from the external device to the user terminal may be in a ciphered form.

According to an embodiment, the method further comprises verifying, by the external device, a role along with the second token received from the user terminal, wherein the read request further includes the role along with the second signature. The role of the second healthcare person is potentially communicated with the read request comprising the second signature by the user terminal. Thus, the external device additionally verifies the role of the second healthcare person along with the second signature before allowing access to the second healthcare person.

According to an embodiment, the method comprises communicating, by the external device, at least a portion of the updated patient information that includes the stored patient information and the first information in accordance with the role, based on a successful verification of the role along with the second token. The updated patient information communicated by the external device therefore, depends on the role of the second healthcare person. The second healthcare person may only be allowed to access a portion of the updated patient information on a need-to-know basis or complete patient information based on the role, for example, a nurse or a technician instead of a doctor.

According to an embodiment, the second healthcare person may also want to write new information at another time instant. In this regard, the external device is configured to receive a write request initiated by the second healthcare person from the user terminal when the user terminal is within a proximal communication range of the external device. The external device thus, verifies the write request based on at least the second signature, the role, the public key of the user terminal, or a validity of the access token (as time-bound validity may be expired), if provided, in the write request. The external device sets a current state of the secured area in the external device as accept state, after successful verification of at least the second signature received in the write request. The user terminal thus communicates the second information, such as a newly inputted updated patient information, to be added to the previous patient information in the external device.

According to an embodiment, the method further comprises communicating, by the user terminal, the updated patient information along with signatures to the server system for verification when a network connectivity with the server system is established. Optionally, the updates to the stored patient information are incrementally stored (or appended) in the external device but original stored information on the external device remains unchanged. The first signature and the second signature may potentially be used to trace the origin of updates in the patient information. When the server system connectivity is available, the user terminal communicates the updated patient information to the server system. Therefore, the server system verifies the updated patient information based on the first signature and the second signature, the timestamps, and the roles of the healthcare persons based on the most current authorization vectors and authentication information available on the server system.

In a token-based verification process, the external device may use a token (T) for authorization until the token is valid, i.e., limited at least by an expiration time. Furthermore, if the token is invalid, for example, when the token exceeds the expiration time, a signature (e.g. as described in the signature-based verification process) is used for the authorization. The token-based verification process is described below.

According to embodiment, the method comprises creating a first key pair, such as one key of the first key pair is a public key (PKserver), whereas other key of the first key pair is a secret key (SKserver), which are created by the server system. The server system holds (i.e. stores) the created public key and the secret key. A program code on the external device receives the public key of the server system upon initialisation. The pre-installed application in the user terminal creates a second key pair comprising a session public key (PKsession) and a session secret key (SKsession). The user terminal stores the secret key in the secured area, such as a key store or a keychain. The keys in the first key pair and the second key pair are used for binding the token (T) to the user device.

According to an embodiment, the method further comprises executing, by the user terminal, login to the server system using login credentials. This is done in order to obtain the first token. The identification medium, such as the first identification medium is used to provide login credentials to server system, when the identification medium is presented to the user terminal. Optionally, other kind of credentials may be used like combination of a username of the first healthcare person and a password associated therewith. In an example, the login credentials may also include the aforementioned device credentials. Furthermore the embodiment comprises receiving, by the user terminal, a first token from the server system in response to a successful verification of the login credentials by the server system, wherein the first token includes at least an expiration time, a unique identity of the first healthcare person, and a signature created using a secret key of the server system. The server system communicates the token to the user terminal after successful verification of the login credentials for authorization purposes. Additionally, and optionally, for additional protection, the token may be encrypted using the public key of the second key pair or the public key provided by the first identification medium. Thus, the encrypted token needs to be decrypted with a corresponding secret key, such as the secret key of the second key pair before using the token.

According to an embodiment, the method further comprises receiving, by the user terminal, a user input of new information related to the patient via an application in the user terminal. Once the token is received, the first healthcare person may input the new information to be send later via the application of the user terminal.

According to an embodiment, the method further comprises communicating, by the user terminal, the token received from the server system to the external device for verification. The user terminal is configured to further communicate the token to the external device to initiate verification by the external device using the token in the token-based verification process to allow reading existing information or writing new information to the external device.

According to an embodiment, the method further comprises verifying, by the external device, the token communicated by the user terminal based on at least a public key of the server system, wherein the public key is stored in the external device. The verification of the token may be performed by using the public key of the first key pair created by the server system. The public key is already stored in the external device which was received at the time of initialisation of the program code on the external device.

According to an embodiment, the method further comprises setting, by the external device, a current state of a secured area in the external device to a data write accept state based on a successful verification of the first token. The current state of a secured area in the external device is set to data write accept state after successful verification of the token, such that the external device allows the user input of the new information related to the patient to be written in the secured area therein.

According to an embodiment, the method further comprises communicating, by the user terminal, the new information that is signed using the first secret key to the external device based the set data write accept state. The user terminal thus communicates the new information as a new update to be stored in the external device. Additionally, the signatures, such as the first signature or the second signature may be used, for example, for non-repudiation purposes by generating the signatures and storing the signatures with the patient information on the external device.

In an exemplary scenario, a healthcare person requests to read the patient information from the external device using the token for authorization. The read request is sent to the program code installed on the external device. If successfully authorized, a signature over the patient information and potentially, the signature associated with the healthcare person is sent to the application pre-installed in the user terminal. Further, the patient information and the signature are potentially sent to the server system for later use. Additionally, if the signature over the patient information is present, the signature is potentially used for non-repudiation or any other purposes needed by the server system. In a case where the identification medium is software, a chip, or a circuitry and integrated to the user terminal, the user terminal maintains (i.e. persists or stores) a key pair generated by the identification medium and stores a secret key of the key pair generated by the identification medium in the secure area within the user terminal. Thus, the secret key may be used by prompting a healthcare person to provide his/her user credentials, such as a password, PIN, or biometric, to be verified by the user terminal.

DETAILED DESCRIPTION OF THE DRAWINGS

Referring to FIG. 1A, illustrated is a block diagram of a system 100A to secure sensitive information, in accordance with an embodiment of the present disclosure. As illustrated, the system 100A comprises a user terminal 102, a server system 104, a first identification medium 106, and an external device 108. In this case, the first identification medium 106 is an independent hardware device. However, it is to understood that the first identification medium 106 may be integrated with the user terminal 102. The external device 108 is configured to store patient information in a designated secured area. Moreover, the user terminal 102 is communicatively coupled to the external device 108 and the server system 104. As shown, the server system 104 provides all backend functionalities needed for logical operations, data storage and long-distance communications. The user terminal 102 is configured to obtain a first token from a server system (104) and a first signature generated using a first secret key inside a first identification medium 106, wherein the first secret key is associated with a first healthcare person. Furthermore, the user terminal 102 is configured to communicate a write request that includes at least the first signature and the first token to the external device 108. The external device 108 is configured to receive the write request from the user terminal 102 when the user terminal 102 is within a proximal communication range of the external device 108. Moreover, the external device 108 is configured to verify at least the first token received in the write request. Furthermore, the user terminal 102 is further configured to write first information to the external device 108, based on verification of at least the first token.

Figure 1B:
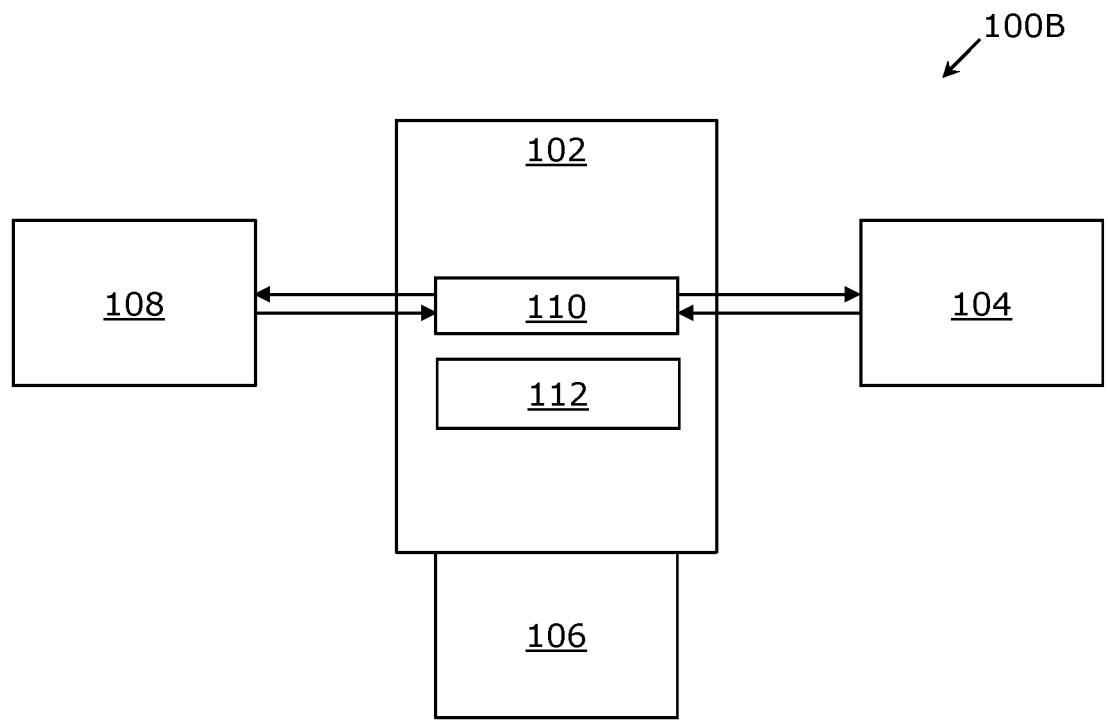
FIG. 1B is a block diagram of a system to secure sensitive information, in accordance with another embodiment of the present disclosure.

Referring to FIG. 1B, illustrated is a block diagram of a system 100B to secure sensitive information, in accordance with an embodiment of the present disclosure. As illustrated, the system 100B comprises the user terminal 102, the external device 108, the server system 104 and the first identification medium 106. The user terminal 102 further comprises a communication interface 110 and an application 112. The user terminal 102 is communicatively coupled to the external device 108 and the server system 104 via the communication interface 110. The communication interface 110 facilitates a short-range communication, such as via NFC and Wi-Fi. The application 112 provide a user interface and necessary logical structure, to process the sensitive information.

Figure 2:
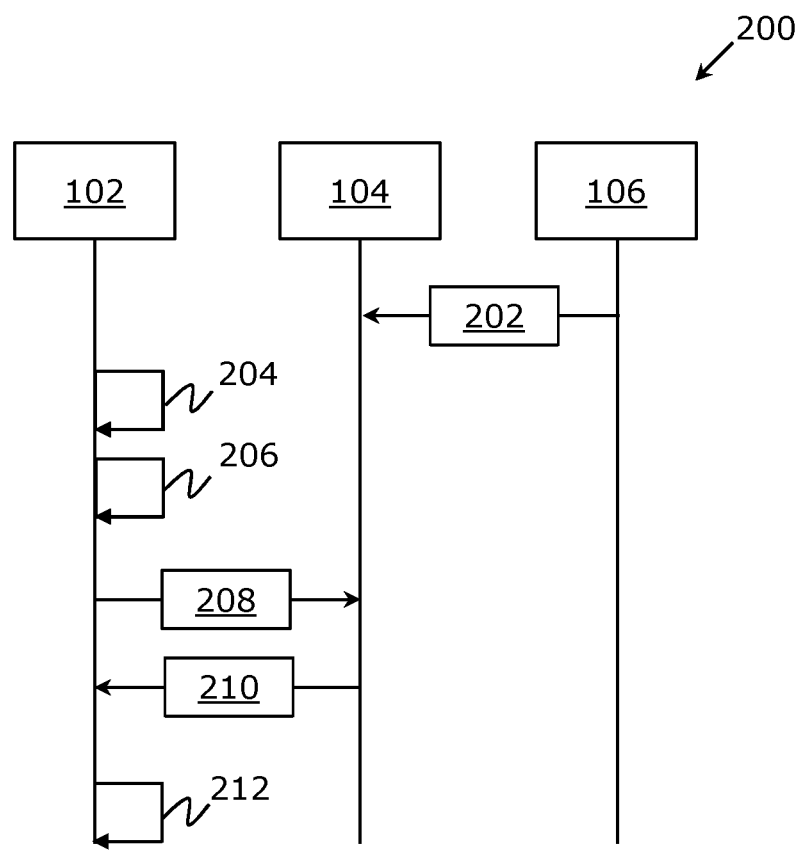
FIG. 2 is a flow diagram that depicts an exemplary registration process of a user terminal to a server system, in accordance with an embodiment of the present disclosure.

Referring to FIG. 2, illustrated is a flow diagram 200 that depicts an exemplary registration process of the user terminal 102 to the server system 104, in accordance with an embodiment of the present disclosure. The communication between the user terminal 102, the server system 104 and the first identification medium 106 for registration purpose, is shown. At a step 202, the server system 104 registers the user identities, such as unique user identifier of the first identification medium 106, that are to access patient information together with the authorization certificates, such as CA and CRL, to authorize decisions. At a step 204, the user terminal 102 generates an asymmetric key pair comprising a public key and a secret key in a registration phase of the user terminal 102 to the server system 104. At a step 206, a unique device ID of the user terminal 102 is derived via a pre-installed application in the user terminal 102. At a step 208, the user terminal 102 is registered by sending the unique device ID or the ID of application created during application setup together with the device public key of the user terminal 102 to the server system 104. At a step 210, the server system 104 responds with the authorization certificates and list of registered user identities to the user terminal 102. At a step 212, the response received from the server system 104 is stored in the user terminal 102.

The steps 202 to 212 are only illustrative and other alternatives can also be provided where one or more steps are added, one or more steps are removed, or one or more steps are provided in a different sequence without departing from the scope of the claims herein.

Figure 3:
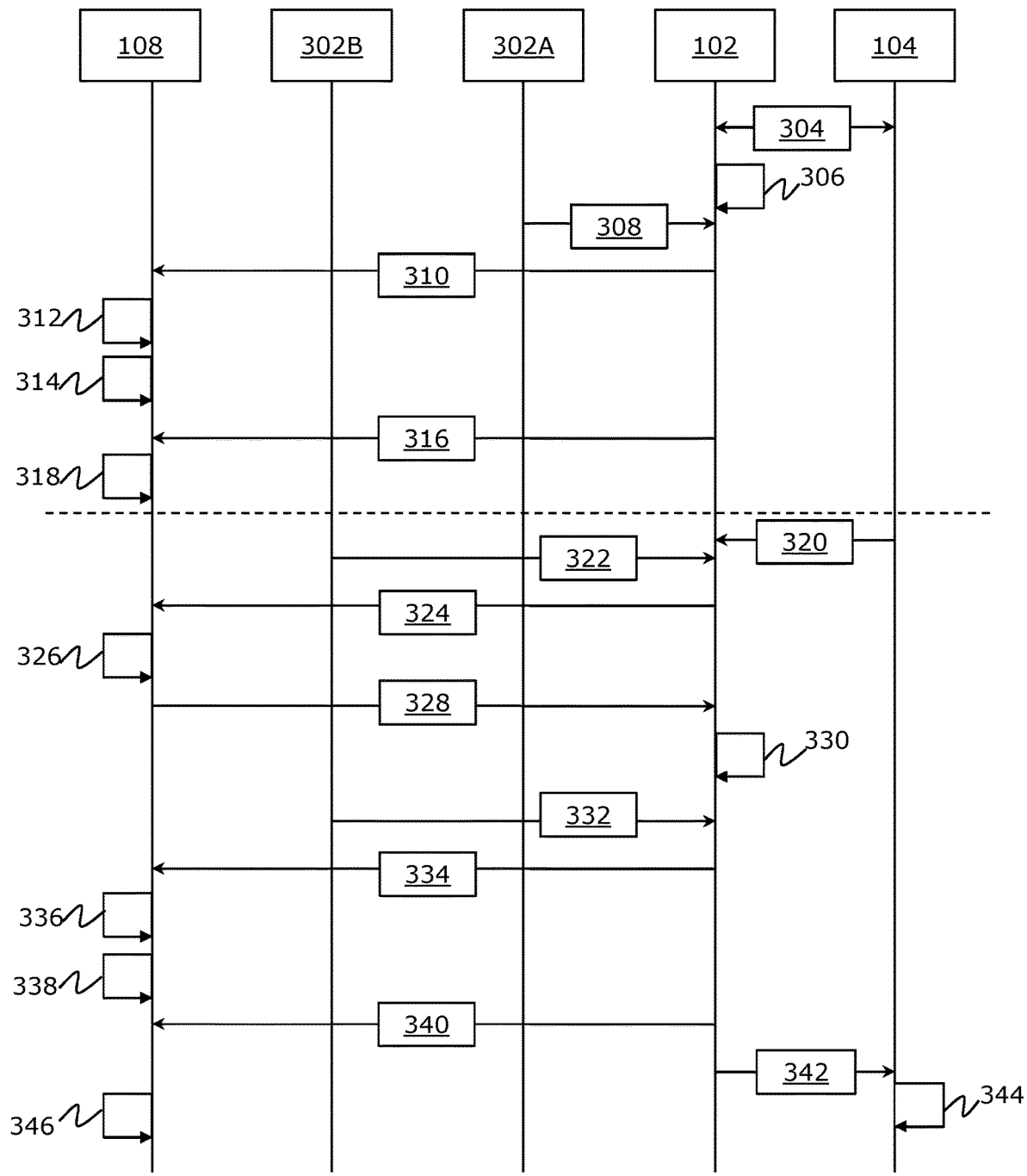
FIG. 3 is a flow diagram that depicts a protocol flow of a system to secure sensitive information using a signature-based authorization, in accordance with an embodiment of the present disclosure.

Referring to FIG. 3, illustrated is a flow diagram 300 that depicts a protocol flow of system using a signature/token-based authorization, in accordance with an embodiment of the present disclosure. As shown, the FIG. 3 depicts the communication between the user terminal 102, the server system 104, a first identification medium 302A, a second identification medium 302B, and the external device 108. At a step 304, user terminal 102 performs login to the server system 104 based on user credentials and/or device credentials. At a step 306, patient information is processed at the user terminal 102 (i.e. input of patient information via an application by the first healthcare person). At a step 308, the user terminal 102 obtains a first signature that is generated using a first secret key which is inside the first identification medium 302A. At a step 310, the user terminal 102 communicates a write request to the external device 108. At a step 312, the external device 108 verifies the received write request based on at least the first signature. Additionally, in an implementation, the write request further includes additional items, such as a role (R) associated with first healthcare person, a public key of the user terminal 102, the authorization certificates, and a unique person identifier (ID_A) associated with the first identification medium 302A together with the first signature. In such a case, such items are also verified. At a step 314, the external device 108 sets a current state of the secured area in the external device 108 as data write accept state, after successful verification of at least the first signature received in the write request. At a step 316, the user terminal 102 sends the first information previously inputted by the first healthcare person via the application to write the first information in the external device. At a step 318, the first information (i.e. the update in the patient information) is stored in the external device 108.

At a step 320, a second healthcare person, using the user terminal 102 performs login to the server system 104 and obtains up-to-date validation data from the server system 104. At a step 322, the user terminal 102 obtains a second signature generated from a second secret key that is inside the second identification medium 302B. At a step 324, the user terminal 102 (based on a user input by the second healthcare person via the application) communicates a read request to access the patient information stored in the external device 108. At a step 326, the external device 108 verifies the read request based on at least the second signature. At a step 328, the external device 108 communicates the updated patient information that includes the stored patient information and the first information to the user terminal for further processing. At a step 330, the user terminal 102 receives a read access to the updated patient information based on role of the second healthcare person. At a step 332, the second signature (S') is fetched from the second identification medium 302B when the second identification medium 302B is presented (i.e. accessible) to the user terminal 102. At a step 334, a write request is initiated by the second healthcare person using the user terminal 102. At a step 336, the external device 108 verifies the write request based on at least the second signature. At a step 338, the external device sets a current state of the secured area in the external device 108 data write accept state, after successful verification of at least the second signature received in the write request. At a step 340, the user terminal 102 writes the second information, such as a new information or update, in the external device 108. At a step 342, the user terminal 102 communicates the updated patient information to the server system 104 for verification. At a step 344, the server system 104 verifies the updated patient information and associated signatures and timestamp of each update. At a step 346, the updated patient information is stored in the external device 108. Alternatively, and optionally, the updated patient information is stored after final verification by the server system 104.

The steps 302 to 344 are only illustrative and other alternatives can also be provided where one or more steps are added, one or more steps are removed, or one or more steps are provided in a different sequence without departing from the scope of the claims herein.

Figure 4:
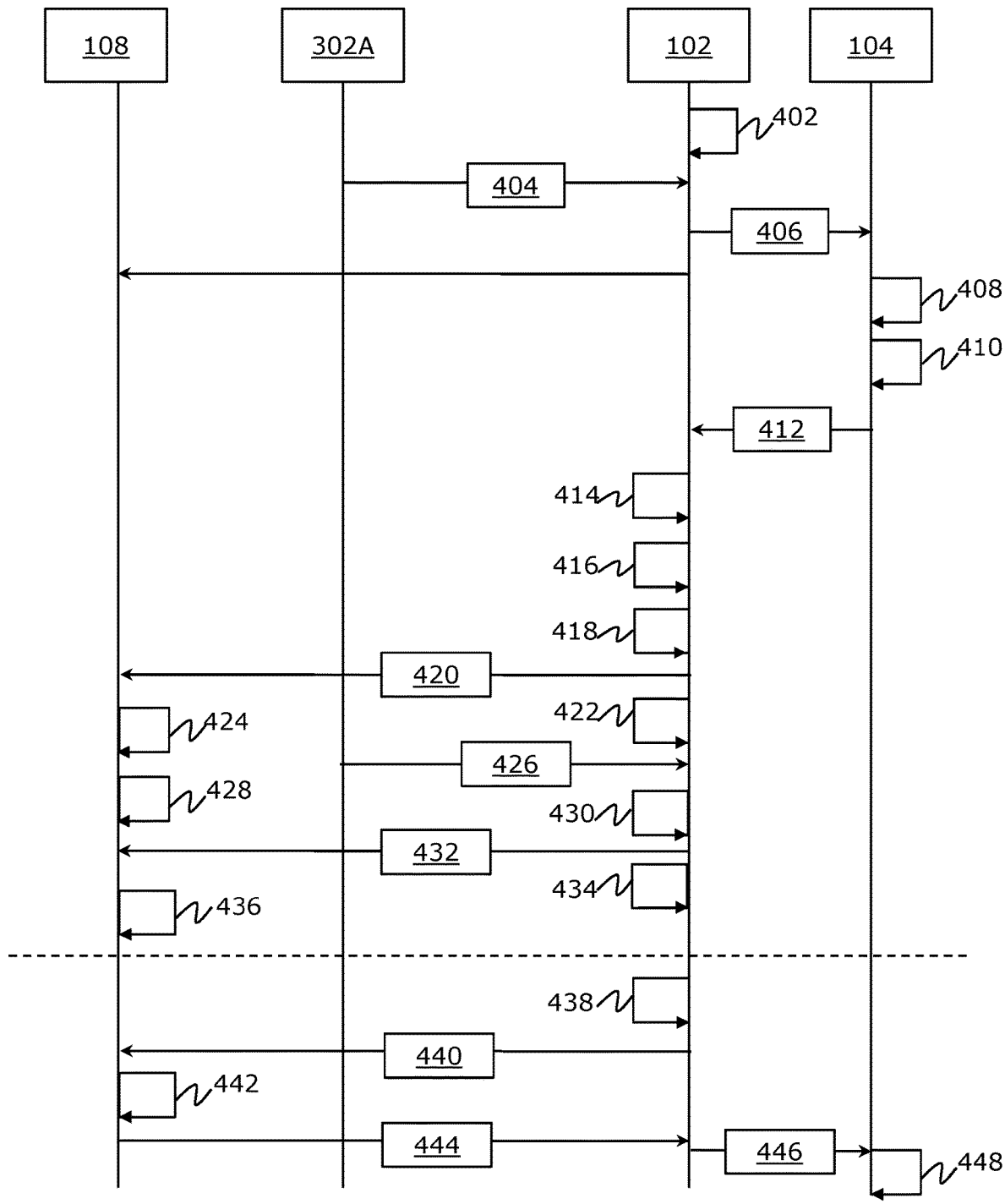
FIG. 4 is a flow diagram depicting protocol flow of a system to secure sensitive information using a token-based authorization, in accordance with an embodiment of the present disclosure.

Referring to FIG. 4, illustrated is a flow diagram 400 depicting protocol flow of system using a token-based authorization, in accordance with an embodiment of the present disclosure. As shown, the FIG. 4 depicts the communication between the user terminal 102, the server system 104, the first identification medium 302A, and the external device 108. At a step 402, the server system 104 creates a first key pair. At a step 404, the first identification medium 302A is presented to the user terminal 102 and a first signature is obtained by the user terminal 102. At a step 406, the user terminal 102 executes login to the server system 104 using login credentials like signature obtained in 404. At a step 408, the server system 104 verifies the login credentials. At a step 410, the server system 104 creates a token. At a step 412, the server system 104 sends the token to the user terminal. The token includes at least an expiration time, a unique identity of the first healthcare person, and a signature created using a secret key of the server system 104. At a step 414, the token is stored in the user terminal 102 after successful verification of the login credentials. The token is optionally stored in a ciphered form. At a step 416, a first healthcare person provides an input of new information via the application of the user terminal 102. At a step 418, the token is deciphered in a case where the token was previously ciphered. At a step 420, the token is communicated to the external device 108 by the user terminal 102. At a step 422, the token is removed from a memory of the user terminal 102. At a step 424, the token is verified by the external device 108 based on a public key of the server system 104. At a step 426, a signature (S) is obtained using a secret key in the first identification medium 302A when the first identification medium 302A is presented and is communicatively coupled to the user terminal 102. At a step 428, the current state of a secured area in the external device 108 is set to data write accept state after successful verification of the token, such that the external device 108 allows the updated patient information to be written therein. At a step 430, the user terminal 102 signs over the updated patient information with the obtained signature (S). At a step 432, the updated patient information is communicated to the external device 108 by the user terminal 102. At a step 434, a public key (PKsession) and a secret key (Sksession) of the second key pair is removed from the user terminal 102. At a step 436, the updated patient information is stored to the external device with the signature S. At a step 438, the secret key of the second key pair is used to decrypt the second token, obtained from the server system based on the second signature lie in steps 404, 406, 408, 410, 412. At a step 440, a read request is communicated by the user terminal 102 to the external device 108 (e.g. read request initiated by using the second token). At a step 442, the read request is verified by the external device 108 based on the second token. At a step 444, the updated patient information with the signature is sent to the user terminal 102 after verification. At a step 446, the patient information is sent to the server system for verification. At a step 448, the updated patient information, the second token and the associated signature (S) is verified by the server system 104.

The steps 402 to 448 are only illustrative and other alternatives can also be provided where one or more steps are added, one or more steps are removed, or one or more steps are provided in a different sequence without departing from the scope of the claims herein.

Figure 5:
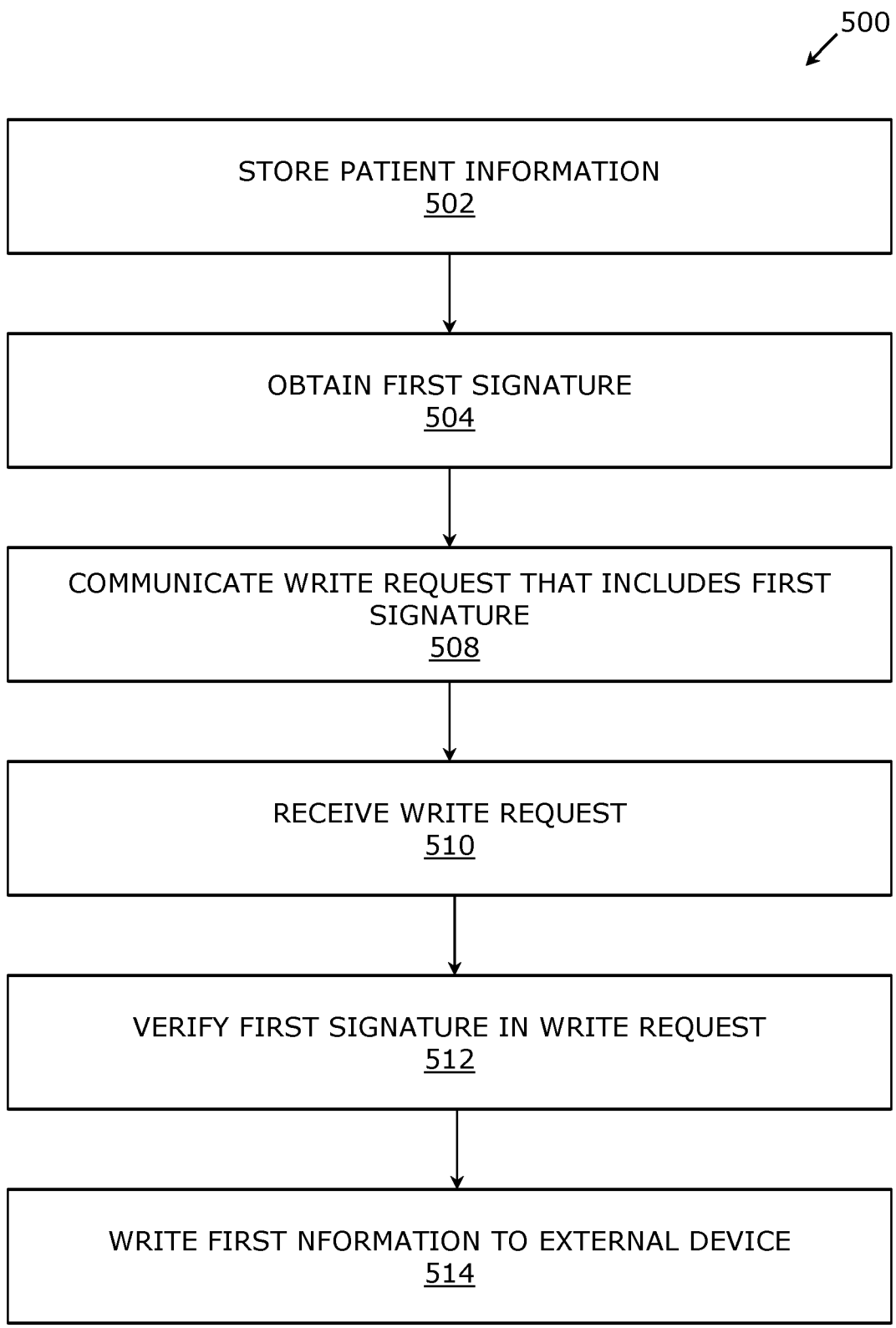
FIG. 5 is a flow diagram depicting steps of a method for securing sensitive information, in accordance with an embodiment of the present disclosure.

Referring to FIG. 5, illustrated is a flow diagram 500 depicting steps of a method for securing sensitive information, in accordance with an embodiment of the present disclosure. At a step 502, the patient information is stored in a secured form in an external device that is carried by a patient. At a step 504, the user terminal obtains a first signature generated using a first secret key inside a first identification medium, wherein the first secret key is associated with a first healthcare person. At a step 506, the user terminal communicates to the external device, a write request that includes at least the first signature. At a step 508, the external device receives the write request from the user terminal when the user terminal is within a proximal communication range of the external device. At a step 510, the external device verifies at least the first signature received in the write request. At a step 512, the user terminal writes first information to the external device, based on verification of at least the first signature.

The steps 502 to 512 are only illustrative and other alternatives can also be provided where one or more steps are added, one or more steps are removed, or one or more steps are provided in a different sequence without departing from the scope of the claims herein.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. A method for securing sensitive information, the method comprising:
   storing patient information in a secured form in an external device that is configured to be carried by a patient;
   obtaining, by a user terminal, a first token from a server system if the server system is available and a first signature generated using a first secret key inside a first identification medium, wherein the first secret key is configured to be associated with a first healthcare person;
   communicating, by the user terminal to the external device, a write request that includes at least the first signature and the first token if the server system was available;
   receiving, by the external device, the write request from the user terminal when the user terminal is within a proximal communication range of the external device;
   performing a verification, by the external device, of the first token received in the write request if the server system was available, otherwise performing a verification of the first signature; and
   writing, by the user terminal, a first information to the external device, based on the verification being successful.

2. The method according to claim 1, further comprising:
   generating, by the user terminal, an asymmetric key pair in a registration phase of the user terminal to the server system; and
   communicating, by the user terminal, a registration request that includes at least one of: a unique device identifier of the user terminal, or an application ID created by an application pre-installed in the user terminal, along with a device public key of the generated asymmetric key pair to the server system over a secured communication channel for registration of the user terminal at the server system.

3. The method according to claim 2, further comprising receiving, by the user terminal, validation data required for authorization decisions from the server system in response to the registration request communicated by the user terminal.

4. The method according to claim 2, further comprising executing a login, by the user terminal, to the server system based on login credentials comprising at least one of: user credentials that includes at least the first signature associated with the first healthcare person, device credentials of the user terminal, or a combination of the user credentials and the device credentials.

5. The method according to claim 4, further comprising receiving, by the user terminal, up-to-date validation data from the server system based on a successful login of the user terminal to the server system, wherein the validation data comprises one or more of: a list of registered user identities, a list of roles of the registered user identities and authorization certificates.

6. The method according to claim 1, further comprising:
   obtaining, by the user terminal, a second token from the server system if the server system is available and a second signature generated using a second secret key that is in a second identification medium, wherein the second secret key is configured to be associated with a second healthcare person; and
   communicating, by the user terminal, a read request to the external device, wherein the read request includes at least the second signature and the second token if the server system was available.

7. The method according to claim 6, further comprising:
   performing a first verification, by the external device, of the second token communicated by the user terminal if the server system was available, otherwise performing a first verification of the second signature; and
   communicating, by the external device, updated patient information that includes the stored patient information and the first information together with the first and second signatures to the user terminal for further processing based on the verification being successful.

8. The method according to claim 6, further comprising:
   performing a second verification, by the external device, of a role received from the user terminal, wherein the read request further includes the role with the second signature; and
   communicating, by the external device, at least a portion of the updated patient information that includes the stored patient information and the first information in accordance with the role, based on the second verification being successful.

9. The method according to claim 7, further comprising communicating, by the user terminal, the updated patient information along with the first and second signatures to the server system for verification when a network connectivity with the server system is established.

10. The method according to claim 1, wherein obtaining the first token comprises:
    executing, by the user terminal, a login to the server system using login credentials;
    receiving, by the user terminal, the first token from the server system in response to a successful verification of the login credentials by the server system, wherein the first token includes at least an expiration time, a unique identity of the first healthcare person, and a signature created using a secret key of the server system.

11. The method according to claim 10, further comprising:
   receiving, by the user terminal, a user input of new information related to the patient via an application in the user terminal;
   communicating, by the user terminal, the first token received from the server system to the external device for verification; and
   verifying, by the external device, the first token communicated by the user terminal based on at least a public key of the server system, wherein the public key is stored in the external device.

12. The method according to claim 11, further comprising setting, by the external device, a current state of a secured area in the external device to a data write accept state based on a successful verification of the first token.

13. The method according to claim 12, further comprising communicating, by the user terminal, the new information that is signed using the first secret key to the external device based the set data write accept state.

14. A system for securing sensitive information, the system comprising:
   an external device configured to store patient information in a secured form, wherein the external device is carried by a patient;
   a user terminal that is configured to:
      obtain a first token from a server system if the server system is available and a first signature generated using a first secret key inside a first identification medium, wherein the first secret key is associated with a first healthcare person;
      communicate a write request to the external device that includes at least the first signature and the first token if the server system was available;
   wherein the external device is configured to:
      receive the write request from the user terminal when the user terminal is within a proximal communication range of the external device; and
      perform a verification of the first token received in the write request if the server system was available, otherwise perform a verification of the first signature; and
      the user terminal is further configured to write a first information to the external device, based on the verification of at least the first tokenbeing successful.

15. A computer program product comprising a non-transitory computer-readable storage medium having computer-readable instructions stored thereon, the computer-readable instructions being executable by a computerized device comprising processing hardware to execute a method as claimed in claim 1.

16. The system of claim 14, wherein the user terminal is further configured to:
   obtain a second token from the server system if the server is available and a second signature generated using a second secret key that is in a second identification medium, wherein the second secret key is configured to be associated with a second healthcare person; and
   communicate a read request to the external device, wherein the read request includes at least the second signature and the second token if the server system was available.

17. The system of claim 16, wherein the external device is further configured to:
   perform a first verification of the second token communicated by the user terminal if the server system was available, otherwise perform a first verification of the second signature; and
   communicate updated patient information that includes the stored patient information and the first information together with the first and second signatures to the user terminal for further processing based on the verification being successful.

18. The system of claim 16, wherein the external device is further configured to:
   perform a second verification of a role received from the user terminal, wherein the read request further includes the role with the second signature; and
   communicate to the user terminal at least a portion of the updated patient information that includes the stored patient information and the first information in accordance with the role, based on the second verification being successful.

* * * * *